(12) United States Patent
Lee et al.

(10) Patent No.: US 8,889,804 B2
(45) Date of Patent: Nov. 18, 2014

(54) METHOD FOR PREPARING POLYPROPYLENE USING TRANSITION METAL COMPOUND CONTAINING THIOPHENE-FUSED CYCLOPENTADIENYL LIGAND

(75) Inventors: Bun-Yeoul Lee, Gyeonggi-do (KR); Ji-Hae Park, Gyeonggi-do (KR); Seung-Hyun Do, Gyeonggi-do (KR); Hwa-Kyu Kim, Daejeon (KR); Jae-Young Park, Daejeon (KR); Seung-Woong Yoon, Daejeon (KR)

(73) Assignee: Lotte Chemical Corporation, Seoul (KR)

( * ) Notice: Subject to any disclaimer, the term of this patent is extended or adjusted under 35 U.S.C. 154(b) by 63 days.

(21) Appl. No.: 13/640,872

(22) PCT Filed: Apr. 12, 2011

(86) PCT No.: PCT/KR2011/002584
§ 371 (c)(1),
(2), (4) Date: Apr. 23, 2013

(87) PCT Pub. No.: WO2011/129593
PCT Pub. Date: Oct. 20, 2011

(65) Prior Publication Data
US 2013/0211021 A1 Aug. 15, 2013

(30) Foreign Application Priority Data

Apr. 12, 2010 (KR) .................. 10-2010-0033273
Jun. 16, 2010 (KR) .................. 10-2010-0057102

(51) Int. Cl.
| | | |
|---|---|---|
| *C08F 4/6592* | (2006.01) | |
| *C08F 4/642* | (2006.01) | |
| *C08F 4/643* | (2006.01) | |
| *C08F 110/06* | (2006.01) | |
| *C07D 409/04* | (2006.01) | |
| *B01J 31/02* | (2006.01) | |
| *C08F 236/04* | (2006.01) | |
| *C07F 7/28* | (2006.01) | |
| *C07F 17/00* | (2006.01) | |
| *C08F 10/02* | (2006.01) | |
| *C08F 210/16* | (2006.01) | |
| *C08F 4/659* | (2006.01) | |
| *C08F 10/00* | (2006.01) | |

(52) U.S. Cl.
CPC ............ *C08F 4/6592* (2013.01); *C07D 409/04* (2013.01); *B01J 31/0244* (2013.01); *C08F 4/65908* (2013.01); *C08F 236/04* (2013.01); *C07F 7/28* (2013.01); *C08F 2420/06* (2013.01); *C07F 17/00* (2013.01); *C08F 2420/02* (2013.01); *C08F 10/02* (2013.01); *C08F 10/00* (2013.01); *C08F 210/16* (2013.01); *C08F 4/65912* (2013.01); *Y10S 526/943* (2013.01)

USPC ........... 526/161; 526/160; 526/351; 526/943; 502/103; 502/153; 502/155

(58) Field of Classification Search
CPC ............ C08F 4/65908; C08F 4/65912; C08F 4/6592; C08F 110/06
USPC .......... 526/160, 161, 351, 943; 502/103, 152, 502/155
See application file for complete search history.

(56) References Cited

U.S. PATENT DOCUMENTS

| | | |
|---|---|---|
| 6,451,938 B1 | 9/2002 | Fisher et al. |
| 6,635,779 B1 | 10/2003 | Ewen et al. |
| 2004/0242880 A1† | 12/2004 | Mihan |
| 2005/0192418 A1† | 9/2005 | Ewen |
| 2005/0234204 A1 | 10/2005 | Resconi et al. |
| 2007/0010637 A1 | 1/2007 | Lee et al. |
| 2007/0010638 A1 | 1/2007 | Lee et al. |
| 2007/0225158 A1 | 9/2007 | Lee et al. |
| 2007/0260026 A1 | 11/2007 | Michiue et al. |
| 2008/0027071 A1 | 1/2008 | Rottlander et al. |
| 2010/0062927 A1† | 3/2010 | Lee |
| 2010/0093959 A1 | 4/2010 | Hong et al. |
| 2010/0130201 A1 | 5/2010 | Yu |
| 2013/0203949 A1 | 8/2013 | Lee et al. |
| 2013/0211020 A1 | 8/2013 | Lee et al. |
| 2013/0211023 A1 | 8/2013 | Lee |
| 2013/0211024 A1 | 8/2013 | Lee et al. |

FOREIGN PATENT DOCUMENTS

| | | |
|---|---|---|
| CN | 1310909 C | 4/2007 |
| CN | 101578293 A | 11/2009 |
| EP | 0 892 013 A1 | 1/1999 |
| EP | 1 739 103 A1 | 1/2007 |

(Continued)

OTHER PUBLICATIONS

Park et al., "Preparation of half-metallocene of thiophene-fused and tetrahydroquinoline-linked cyclopentadienyl ligands for ethylene/olefin copolymerization", Dalton Trans., 2010, 39, 9994-10002.*
International Search Report for corresponding International Application No. PCT/KR2011/002584 (6 pages).
Ryabov, Alexey N. et al., "Zirconium Complexes with Cyclopentadienyl Ligands Involving Fused a Thiophene Fragment", Organometallics, vol. 21, pp. 2842-2855, dated Jun. 8, 2002 (14 pages).
Katritzky, A. R. et al., α-*Metallation of Tetrahydroquinoline and Indoline via their Lithium Carbamates: A Versatile One-Pot Procedure*, J. Chem. Soc. Perkin Trans. (1989) 17-19.

(Continued)

*Primary Examiner* — Caixia Lu
(74) *Attorney, Agent, or Firm* — Alston & Bird LLP

(57) ABSTRACT

The present invention relates to a preparation method for polypropylene that comprises polymerizing a propylene monomer in the presence of a catalyst comprising a novel transition metal compound. Using the novel transition metal compound as a catalyst, the preparation method for polypropylene according to the present invention can not only acquire high catalytic activity for polymerization to achieve high efficiency of the process but allow it to easily control the fine-structure characteristics of the polymer, thereby providing polypropylene having desired properties with ease.

10 Claims, No Drawings

(56) References Cited

FOREIGN PATENT DOCUMENTS

| | | |
|---|---|---|
| JP | 2001-512523 A | 8/2001 |
| JP | 2003-517010 A | 5/2003 |
| JP | 2005-538198 A | 12/2005 |
| JP | 2006-502076 A | 1/2006 |
| JP | 2006-513974 A | 4/2006 |
| JP | 2008-527050 A | 7/2008 |
| JP | 2008-222635 A | 9/2008 |
| KR | 10-0354290 B1 | 1/2001 |
| KR | 10-2007-0096465 A | 10/2007 |
| KR | 10-0789241 B1 | 1/2008 |
| KR | 10-0789242 B1 | 1/2008 |
| KR | 10-0820542 B1 | 4/2008 |
| KR | 10-2008-0049981 A | 6/2008 |
| KR | 10-2008-0065868 A | 7/2008 |
| KR | 10-0843603 B1 | 7/2008 |
| KR | 10-2008-0070989 A | 8/2008 |
| KR | 10-2008-0101542 A | 11/2008 |
| KR | 10-0906165 B1 | 7/2009 |
| KR | 10-2010-0033273 A | 3/2010 |
| KR | 10-2010-0057102 A | 5/2010 |
| WO | WO-03/024982 A1 | 3/2003 |
| WO | WO-2006/022355 A | 3/2006 |
| WO | WO 2008-066266 A1 | 6/2008 |
| WO | WO 2008-084931 A1 | 7/2008 |

OTHER PUBLICATIONS

Cho, D. J., et al.; "o-Phenylene-Bridged Cp/Amido Titanium Complexes for Ethylene/1-Hexene Copolymerizations;" Organometallics, vol. 25, No. 9; pp. 2133-2134; dated Apr. 24, 2006; abstract retrieved on May 27, 2014 from <http://pubs.acs.org/doi/abs/10.1021/om0601854>.

De Rosa, C., et al.; "Metalloorganic Polymerization Catalysis as a Tool to Probe Crystallization Properties of Polymers: The Case of Isotactic Poly(1-butene);" Angew. Chem. Int. Ed., vol. 48, No. 52; pp. 9871-; dated Dec. 21, 2009; abstract retrieved on May 28, 2014 from <http://onlinelibrary.wiley.com/doi/10.1002/anie.200904300/abstract>.

De Rosa, C., et al.; "Structure—Property Correlations in Polypropylene from Metallocene Catalysts: Stereodefective, Regioregular Isotactic Polypropylene;" J. Am. Chem. Soc., vol. 126, No. 51; pp. 17040-17049; dated Dec. 29, 2004; abstract retrieved on May 28, 2014 from <http://pubs.acs.org/doi/abs/10.1021/ja045684f>.

De Rosa, C., et al.; "Synthesis and Characterization of High-Molecular-Weight Syndiotactic Amorphous Polypropylene;" J. Am. Chem. Soc., vol. 125, No. 36; pp. 10913-10920; dated Sep. 10, 2003; abstract retrieved on May 28, 2014 from <http://pubs.acs.org/doi/abs/10.1021/ja035911y>.

Ewen, J. A., et al. "Chiral Ansa Metallocenes with Cp Ring-Fused to Thiophenes and Pyrroles: Syntheses, Crystal Structures, and Isotactic Polypropylene Catalysts;" J. Am. Chem. Soc.,vol. 123, No. 20; pp. 4763-4773; dated May 23, 2001; abstract retrieved on May 28, 2014 from <http://pubs.acs.org/doi/abs/10.1021/ja004266h>.

Ewen, J. A., et al.; "Polymerization Catalysts with Cyclopentadienyl Ligands Ring-Fused to Pyrrole and Thiophene Heterocycles;" J. Am. Chem. Soc., vol. 120, No. 41; pp. 10786-10787; dated Oct. 21, 1998; abstract retrieved on May 28, 2014 from <http://pubs.acs.org/doi/abs/10.1021/ja9823215>.

Ewen, J. A., et al.; "Stereoblock Isotactic-Hemiisotactic Poly(propylene)s and Ethylene/Propylene Copolymers Obtained with ansa-Cyclopenta[1,2-b;4,3-b']dithiophene Catalysts;" Macromol. Chem. Phys., vol. 205, No. 3; pp. 302-307; dated Feb. 2004; abstract retrieved on May 28, 2014 from <http://onlinelibrary.wiley.com/doi/10.1002/macp.200300222/abstract>.

Grandini, C., et al.; "Heterocycle-Fused Indenyl Silyl Amido Dimethyl Titanium Complexes as Catalysts for High Molecular Weight Syndiotactic Amorphous Polypropylene;" Organometallics, vol. 23, No. 3; pp. 344-360; dated Feb. 2, 2004; abstract retrieved on May 27, 2014 from <http://pubs.acs.org/doi/abs/10.1021/om030543s>.

Joe, D. J., et al.; "o-Phenylene-bridged Cp/sulfonamido titanium complexes for ethylene/1-octene copolymerization;" Dalton Trans., No. 33; pp. 4056-4062; dated 2006; abstract retrieved on May 27, 2014 from <http://pubs.rsc.org/en/content/articlelanding/2006/dt/b605345a#!divAbstract>.

Joung, U. G., et al.; "Phenylene-Bridged Cp/Carboxamide Ligands for Titanium Complexes of Various Binding Modes and Their Ethylene/1-Octene Copolymerization;" Organometallics, vol. 25, No. 21; pp. 5122-5130; dated Oct. 9, 2006; abstract retrieved on May 27, 2014 from <http://pubs.acs.org/doi/abs/10.1021/om060604x>.

Kaminsky et al.; "New application for metallocene catalysts in olefin polymerization ;" Dalton Trans., No. 41, pp. 8803-8810; dated Aug. 27, 2009; abstract retrieved on May 27, 2014 from <http://pubs.rsc.org/en/content/articlelanding/2009/dt/b910542p#!divAbstract>.

Katritzky, A. R., et al.; "Carbon dioxide: A reagent for the protection of nucleophilic centres and the simultaneous activation of alternative locations to electrophilic attack. : Part I. A new synthetic method for the 2-substitution of 1-unsubstituted indoles;" Tetrahedron Lett., vol. 26, No. 48; pp. 5935-5938; dated 1985; abstract retrieved on May 28, 2014 from <http://www.sciencedirect.com/science/article/pii/S0040403900982650>.

Katritzky A. R., et al.; "Carbon dioxide: A reagent for the protection of nucleophilic centres and the simultaneous activation of electrophilic attack: Part II. A new synthetic method for the 1-substitution of 1,2.3,4-tetrahydroisoquinolines;" Tetrahedron, vol. 42, No. 9; pp. 2571-2574; dated 1986; abstract retrieved on May 28, 2014 from <http://www.sciencedirect.com/science/article/pii/0040402086800242>.

Lee, S. H., et al.; "Bimetallic phenylene-bridged Cp/amide titanium complexes and their olefin polymerization ;" Dalton Trans. No. 40; pp. 4608-4614; dated 2007; abstract retrieved on May 27, 2014 from <http://pubs.rsc.org/en/content/articlelanding/2007/dt/b710017e#!divAbstract>.

Lee, S. H., et al.; "o-Phenylene-bridged Cp/amido titanium and zirconium complexes and their polymerization reactivity;" J. Organomet. Chem. vol. 693, No. 3; pp. 457-467; dated Feb. 1, 2008; abstract retrieved on May 27, 2014 from <http://www.sciencedirect.com/science/article/pii/S0022328X07008297>.

Lee, B. Y., et al.; "Preparation of Anchored Metallocene Complexes on Dehydroxylated Silica and Their Use in the Polymerization of Ethylene;" Macromolecues, vol. 33, No. 9; pp. 3194-3195; dated May 2, 2000; retrieved on May 28, 2014 from <https://www.researchgate.net/publication/231711882_Preparation_of_Anchored_Metallocene_Complexes_on_Dehydroxylated_Silica_and_Their_Use_in_the_Polymerization_of_Ethylene>.

Na, S. J., et al.; "Copolymerization of 5,6-Dihydrodicyclopentadiene and Ethylene;" Macromolecules, vol. 42, No. 11; pp. 4055-4057; dated Jun. 10, 2008; abstract retrieved on May 28, 2014 from <http://pubs.acs.org/doi/abs/10.1021/ma800380r>.

Nifant'ev, A. E., et al.; "C1-Symmetric Heterocyclic Zirconocenes as Catalysts for Propylene Polymerization, 1;" Macromol. Chem. Phys., vol. 205, No. 17; pp. 2275-2291; dated Nov. 26, 2004; abstract retrieved on May 28, 2014 from <http://onlinelibrary.wiley.com/doi/10.1002/macp.200400238/abstract>.

Ryabov, A. N., et al.; "Constrained geometry complexes of titanium (IV) and zirconium (IV) involving cyclopentadienyl fused to thiophene ring", Journal of Organometallic Chemistry, Elsevier-Sequoia S.A. Lausanne, Ch, vol. 690, No. 19, Aug. 5, 2005, pp. 4213-4221, XP027708856, ISSN: 0022-328X [retrieved on Oct. 1, 2005].

Resconi, L., et al.; "C1-Symmetric Heterocyclic Zirconocenes as Catalysts for Propylene Polymerization, 2;" Macromol. Chem. Phys., vol. 206, No. 14; pp. 1405-1438; dated Jul. 21, 2005; abstract retrieved on May 28, 2014 from <http://onlinelibrary.wiley.com/doi/10.1002/macp.200400533/abstract>.

Wu, C. J., et al.; "CO2-Mediated ortho-Lithiation of N-Alkylanilines and Its Use for the Construction of Polymerization Catalysts;" Organometallics, vol. 27, No. 15; pp. 3907-3917; dated Aug. 11, 2008; abstract retrieved on May 27, 2014 from <http://pubs.acs.org/doi/abs/10.1021/om800317v>.

(56) References Cited

OTHER PUBLICATIONS

Wu, C. J., et al.; "*Ortho Lithiation of Tetrahydroquinoline Derivatives and Its [sic] Use for the Facile Construction of Polymerization Catalysts*;" Organometallics, vol. 26, No. 27, Dec. 31, 2007, pp. 6685-6687, Xp008151338.
Wu, C. J., et al.; "*Synthesis and structures of o-phenylene-bridged Cp/phosphinoamide titanium complexes*;" J. Organomet. Chem., vol. 691, No. 26; pp. 5626-5634; dated Dec. 15, 2006; abstract retrieved on May 27, 2014 from <http://www.sciencedirect.com/science/article/pii/S0022328X06007625>.
Yu, S. T., et al.; "*Preparation of a Bulky Cycloolefin/Ethylene Copolymer and Its Tensile Properties*;" Macromolecules, vol. 43, No. 2; pp. 725-730; dated Jan. 26, 2010; abstract retrieved on May 28, 2014 from <http://pubs.acs.org/doi/abs/10.1021/ma902334d>.
Extended European Search Report for Application No. 11769055.2; dated Dec. 10, 2013.
Extended European Search Report for Application No. 11769056.0; dated Dec. 11, 2013.
Extended European Search Report for Application No. 11769059.4; dated Dec. 10, 2013.
Extended European Search Report for Application No. 11769060.2; dated Dec. 10, 2013.
International Preliminary Report on Patentability for Application No. PCT/KR2011/002580; dated Oct. 16, 2012.
International Preliminary Report on Patentability for Application No. PCT/KR2011/002581; dated Oct. 16, 2012.
International Preliminary Report on Patentability for Application No. PCT/KR2011/002583; dated Oct. 16, 2012.
International Preliminary Report on Patentability for Application No. PCT/KR2011/002584; dated Oct. 16, 2012.
International Preliminary Report on Patentability for Application No. PCT/KR2011/002585; dated Oct. 16, 2012.
International Search Report and Written Opinion for Application No. PCT/KR2011/002580; dated Dec. 26, 2011.
International Search Report and Written Opinion for Application No. PCT/KR2011/002581; dated Jan. 19, 2012.
International Search Report and Written Opinion for Application No. PCT/KR2011/002583; dated Jan. 19, 2012.
International Search Report and Written Opinion for Application No. PCT/KR2011/002585; dated Jan. 19, 2012.
International Written Opinion for Application No. PCT/KR2011/002584; dated Jan. 19, 2012.
J. Chem. SC. Perkin Trans. 1989, 16.
Office Action for Chinese Application No. 201180018685.7; dated Dec. 4, 2013.
Office Action for Chinese Application No. 201180018695.0; dated Jan. 6, 2014.
Office Action for Chinese Application No. 201180018710.1; dated Apr. 16, 2014.
Office Action for European Application No. 11769056.0; dated Jan. 7, 2013.
Office Action for European Application No. 11769059.4; dated Jan. 10, 2014.
Office Action for European Application No. 11769060.2; dated Jan. 15, 2014.
Office Action for Japanese Application No. 2013-503703; dated Feb. 4, 2014.
Office Action for Japanese Application No. 2013-504820; dated Feb. 4, 2014.
Office Action for Korean Application No. 10-2011-0033623; dated Apr. 1, 2014.
Office Action for Korean Application No. 10-2011-0033625; dated Apr. 1, 2014.
Office Action for Korean Application No. 10-2011-0033626; dated Apr. 1, 2014.
Office Action for European Application No. 11 769 056.0 dated Sep. 17, 2014.
Office Action for European Application No. 11 769 058.0 dated Sep. 17, 2014.
Office Action for European Application No. 11 769 060.0 dated Sep. 17, 2014.
Office Action for European Application No. 11 769 055.0 dated Sep. 17, 2014.
Office Action for European Application No. 11 769 059.0 dated Sep. 17, 2014.
Bryliakov, K. P. et al., *Nasa-Titanocene Catalysts for Alpha-Olefin Polymerization, Syntheses, Structures, and Reactions with Methylaluminoxane and Boron-Based Activators*, Organometallics, ACS, vol. 24, No. 5 (Feb. 28, 2005), pp. 894-904 (XP00904851).
Taichi Senda et al. Titanium Complexes of Silicon-Bridged . . . 1-Hexene, Dec. 4, 2009, World Wide Web.†

\* cited by examiner
† cited by third party

METHOD FOR PREPARING POLYPROPYLENE USING TRANSITION METAL COMPOUND CONTAINING THIOPHENE-FUSED CYCLOPENTADIENYL LIGAND

FIELD OF THE INVENTION

The present invention relates to a method for preparing a polypropylene using a transition metal compound containing a thiophene-fused cyclopentadienyl ligand.

BACKGROUND OF THE INVENTION

Depending on the stereo-structure, polypropylene is classified into isotactic polypropylene (hereinafter, referred to as "iPP"), syndiotactic polypropylene (hereinafter, referred to as "sPP"), and atactic polypropylene (hereinafter, referred to as "aPP").

Relative to the iPP and sPP which have good mechanical properties and thermal characteristics and thus have been actively exploited, the aPP is still undeveloped in terms of commercial use due to its low isotacticity and consequent limitation in enhancement of properties.

The aPP can be isolated as a by-product during the recovery of an aliphatic solvent in the slurry process for preparation of iPP, or prepared in the presence of a heterogeneous catalyst containing a modified titanium (III) chloride and an organoaluminum compound, such as diethyl aluminum chloride, as a co-catalyst or an activator. However, the iPP process with improved isotacticity cannot yield an amorphous aPP as a by-product but needs the addition of a co-monomer even when a PP with low crystallinity is produced according to the use purpose.

There has recently been a suggestion to a method for preparing an aPP with narrow molecular weight distribution using a variety of metallocene catalyst systems. The metallocene catalyst systems useful in this method are, for example, (a) an achiral, unbridged metallocene or stereo-rigid C2v symmetric metallocene catalyst, (b) meso-isomeric ansa metallocene catalyst, (c) an ansa-C2 symmetric metallocene catalyst with a bridge at 2,2'-position of the indenyl ring, and (d) a catalyst of monoCp compound.

The properties of the aPP greatly change according to the molecular weight of the aPP. For example, the aPP with a weight average molecular weight below 15,000 is sticky at the room temperature and thus has a limitation in its use, consequently with low applicability as a polymer material.

Further, the conventional metallocene catalyst systems have a low catalytic activity for polymerization to prepare a polypropylene and require a relatively low polymerization temperature (for example, 20° C. or below) enough to acquire an aPP with high molecular weight.

DISCLOSURE OF INVENTION

Technical Problem

It is therefore an object of the present invention to provide a method for preparing a polypropylene using a catalyst having high catalytic activity and providing an aPP with high molecular weight.

Technical Solution

To achieve the object of the present invention, there is provided a method for preparing a polypropylene that comprises polymerizing a propylene monomer in the presence of a catalyst comprising a transition metal compound represented by the following formula 1:

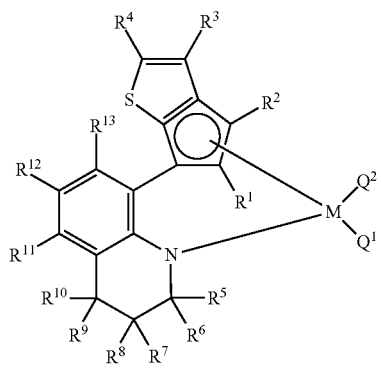

[Formula 1]

In the formula 1, M is a Group 4 transition metal; $Q^1$ and $Q^2$ are independently a halogen, $C_1$-$C_{20}$ alkyl, $C_2$-$C_{20}$ alkenyl, $C_2$-$C_{20}$ alkynyl, $C_6$-$C_{20}$ aryl, $C_1$-$C_{20}$ alkyl $C_6$-$C_{20}$ aryl, $C_6$-$C_{20}$ aryl $C_1$-$C_{20}$ alkyl, $C_1$-$C_{20}$ alkylamido, $C_6$-$C_{20}$ arylamido, or $C_1$-$C_{20}$ alkylidene;

$R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to form a ring; and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

In the transition metal compound of the formula 1, M is titanium (Ti), zirconium (Zr), or hafnium (Hf); $Q^1$ and $Q^2$ are independently methyl or chlorine; $R^1$, $R^2$, $R^3$, $R^4$, and $R^5$ are independently hydrogen or methyl; and $R^6$, $R^7$, $R^8$, $R^9$, $R^{10}$, $R^{11}$, $R^{12}$, and $R^{13}$ are independently hydrogen.

The catalyst may further comprise at least one co-catalyst compound selected from the group consisting of compounds represented by the following formula 6, 7, or 8.

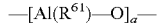

[Formula 6]

In the formula 6, $R^{61}$ is independently a halogen radical, a $C_1$-$C_{20}$ hydrocarbyl radical, or a halogen-substituted $C_1$-$C_{20}$ hydrocarbyl radical; and a is an integer of 2 or above.

[Formula 7]

In the formula 7, D is aluminum (Al) or boron (B); and $R^{71}$ is independently a halogen radical, a $C_1$-$C_{20}$ hydrocarbyl radical, or a halogen-substituted $C_1$-$C_{20}$ hydrocarbyl radical.

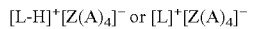

[Formula 8]

In the formula 8, L is a neutral or cationic Lewis acid; Z is a Group 13 element; and A is independently a $C_6$-$C_{20}$ aryl or $C_1$-$C_{20}$ alkyl radical having at least one hydrogen atom substituted with a halogen radical, a $C_1$-$C_{20}$ hydrocarbyl radical, a $C_1$-$C_{20}$ alkoxy radical, or a $C_6$-$C_{20}$ aryloxy radical.

As for the co-catalyst compound, in the formula 6, $R^{61}$ is methyl, ethyl, n-butyl, or isobutyl. In the formula 7, D is aluminum, and $R^{71}$ is methyl or isobutyl; or D is boron, and $R^{71}$ is pentafluorophenyl. In the formula 8, $[L-H]^+$ is a dimethylanilinium cation, $[Z(A)_4]^-$ is $[B(C_6F_5)_4]^-$, and $[L]^+$ is $[(C_6H_5)_3C]^+$.

The content of the co-catalyst compound is given such that the molar ratio of a metal in the co-catalyst compound with respect to one mole of a transition metal in the transition metal compound of the formula 1 is 1:1 to 1:100,000.

Further, the catalyst may comprise the transition metal compound of the formula 1 bound to at least one support selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2$—$TiO_2$—MgO, bauxite, zeolite, starch, and cyclodextrine.

The polymerization may be carried out under conditions of −50 to 500° C. and 1 to 3,000 atm.

The polypropylene may have a weight average molecular weight of 20,000 to 1,000,000; and a density of 0.8 to 0.9 g/ml.

Further, the polypropylene may have an isotacticity (Pentad I.I, mmmm) of 5 to 20%.

Advantageous Effects

Using a novel transition metal compound as a catalyst, the preparation method for polypropylene according to the present invention can not only acquire high catalytic activity for polymerization to achieve high efficiency of the process but easily control the fine-structure characteristics of the polymer, thereby providing polypropylene having desired properties with ease.

DETAILED DESCRIPTION OF THE INVENTION

Hereinafter, a description will be given as to a method for preparing a polypropylene according to the embodiments of the present invention.

In the course of repeated studies on the catalysts for olefin polymerization, the inventors of the present invention have found out a novel ligand in which an amido ligand is linked to an ortho-phenylene ligand to form a condensed ring, and a 5-membered cyclic pi-ligand linked to the ortho-phenylene ligand is fused with a heterocyclic thiophene ligand. Also, they have found it out that a transition metal compound comprising the ligand exhibits higher catalytic activity and provides a polymer with higher molecular weight than a transition metal compound not fused with a heterocyclic thiophene ligand.

Particularly, it has been revealed that the use of the transition metal compound comprising the novel ligand in the preparation of polypropylene (preferably, aPP) makes it easier to control the fine-structure characteristics of the copolymer and thus allows the preparation of a polypropylene with high molecular weight, thereby completing the present invention.

In accordance with one embodiment of the present invention, there is provided a method for preparing a polypropylene that comprises polymerizing a propylene monomer in the presence of a catalyst comprising a transition metal compound represented by the following formula 1:

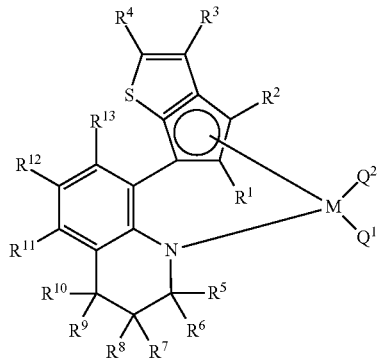

[Formula 1]

In the formula 1, M is a Group 4 transition metal;

$Q^1$ and $Q^2$ are independently a halogen, $C_1$-$C_{20}$ alkyl, $C_2$-$C_{20}$ alkenyl, $C_2$-$C_{20}$ alkynyl, $C_6$-$C_{20}$ aryl, $C_1$-$C_{20}$ alkyl $C_6$-$C_{20}$ aryl, $C_6$-$C_{20}$ aryl $C_1$-$C_{20}$ alkyl, $C_1$-$C_{20}$ alkylamido, $C_6$-$C_{20}$ arylamido, or $C_1$-$C_{20}$ alkylidene;

$R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to form a ring; and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

Firstly, the catalyst used in the preparation method of the present invention will be described.

The catalyst comprises a transition metal compound represented by the formula 1.

The transition metal composition of the formula 1 is activated with an under-mentioned co-catalyst compound to provide catalytic activity for polymerization reaction of propylene.

The transition metal compound of the formula 1 comprises a novel ligand in which an amido ligand is linked to an ortho-phenylene ligand to form a condensed ring, and a 5-membered cyclic pi-ligand linked to the ortho-phenylene ligand is fused with a heterocyclic thiophene ligand. Accordingly, the transition metal compound exhibits higher catalytic activity for polymerization of propylene than the transition metal compound not fused with a heterocyclic thiophene ligand.

According to the present invention, in the compound of the formula 1, $R^1$, $R^2$, $R^3$, $R^4$, $R^5$, $R^6$, $R^7$, $R^8$, $R^9$, $R^{10}$, $R^{11}$, $R^{12}$, and $R^{13}$ are independently substituted with a substituent, including acetal, ketal, and ether groups. With such substituents, the transition metal compound can be more favored in being supported on the surface of a support.

In the compound of the formula 1, M is preferably titanium (Ti), zirconium (Zr), or hafnium (Hf).

Preferably, $Q^1$ and $Q^2$ are independently halogen or $C_1$-$C_{20}$ alkyl. More preferably, $Q^1$ and $Q^2$ are independently chlorine or methyl.

$R^1$, $R^2$, $R^3$, $R^4$, and $R^5$ are independently hydrogen or $C_1$-$C_{20}$ alkyl, preferably hydrogen or methyl. More preferably, $R^1$, $R^2$, $R^3$, $R^4$, and $R^5$ are independently hydrogen or methyl, with the provision that at least one of $R^3$ and $R^4$ is methyl; and $R^5$ is methyl.

Preferably, $R^6$, $R^7$, $R^8$, $R^9$, $R^{10}$, $R^{11}$, $R^{12}$, and $R^{13}$ are independently hydrogen.

The transition metal compound of the formula 1 preferably includes the above-mentioned substituents with a view to controlling the electronic and steric environments around the metal.

On the other hand, the transition metal compound of the formula 1 can be obtained from a precursor compound represented by the following formula 2:

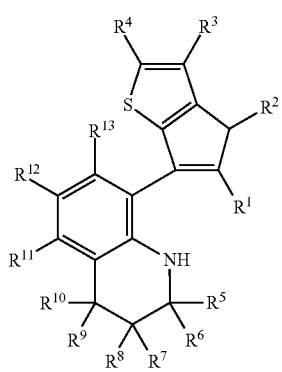

[Formula 2]

In the formula 2, $R^1$, $R^2$, $R^3$, $R^4$, $R^5$, $R^6$, $R^7$, $R^8$, $R^9$, $R^{10}$, $R^{11}$, $R^{12}$ and $R^{13}$ are as defined in the formula 1.

In this regard, the precursor compound of the formula 2 may be prepared by a method comprising: (a) reacting a tetrahydroquinoline derivative represented by the following formula 3 with alkyl lithium and adding carbon dioxide to prepare a compound represented by the following formula 4; and (b) reacting the compound of the formula 4 with alkyl lithium, adding a compound represented by the following formula 5, and then treating with an acid:

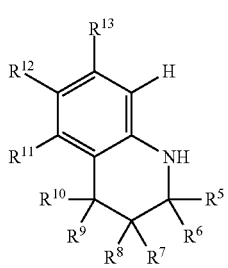

[Formula 3]

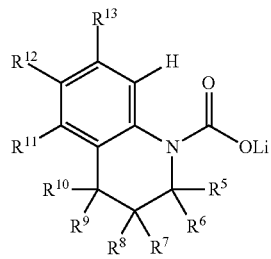

[Formula 4]

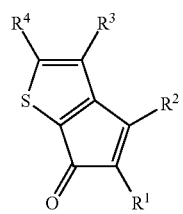

[Formula 5]

In the formulas 3, 4 and 5, $R^1$, $R^2$, $R^3$, $R^4$, $R^5$, $R^6$, $R^7$, $R^8$, $R^9$, $R^{10}$, $R^{11}$, $R^{12}$ and $R^{13}$ are as defined in the formula 1.

In the formulas 3, 4 and 5, $R^1$, $R^2$, $R^3$, $R^4$, and $R^5$ are independently hydrogen or $C_1$-$C_{20}$ alkyl, preferably hydrogen or methyl. More preferably, R', $R^2$, $R^3$, $R^4$, and $R^5$ are independently hydrogen or methyl, with the provision that at least one of $R^3$ and $R^4$ is methyl; and $R^5$ is methyl. Preferably, $R^6$, $R^7$, $R^8$, $R^9$, $R^{10}$, $R^{11}$, $R^{12}$, and $R^{13}$ are independently hydrogen. In this manner, the precursor compound is advantageous in securing easy accessibility and reactivity of a starting material and controlling the electronic and steric environments for the desired transition metal compound of the formula 1.

The step (a) involves reacting a tetrahydroquinoline derivative of the formula 3 with alkyl lithium and then adding carbon dioxide to form a compound of the formula 4, which process can be achieved by the methods disclosed in the known documents (*Tetrahedron Lett.* 1985, 26, 5935; *Tetrahedron* 1986, 42, 2571; and *J. Chem. SC. Perkin Trans.* 1989, 16).

In the step (b), the compound of the formula 4 is reacted with alkyl lithium to activate deprotonation and produce an ortho-lithium compound, which is then reacted with a compound of the formula 5 and treated with an acid to obtain a precursor for transition metal compound of the formula 2.

The method of producing an ortho-lithium compound by reaction between the compound of the formula 4 and alkyl lithium can be understood from known documents (*Organometallics* 2007, 27, 6685; and Korean Patent Registration No. 2008-0065868). In the present invention, the ortho-lithium compound is reacted with a compound of the formula 5 and treated with an acid to produce a precursor for transition metal compound of the formula 2.

The compound of the formula 5 can be prepared by a variety of known methods. For example, the following Scheme 1 can be used to prepare the precursor for the transition metal compound of the present invention with ease in a one-step process, which is economically beneficial by using inexpensive starting materials (*J. Organomet. Chem.*, 2005, 690, 4213).

[Scheme 1]

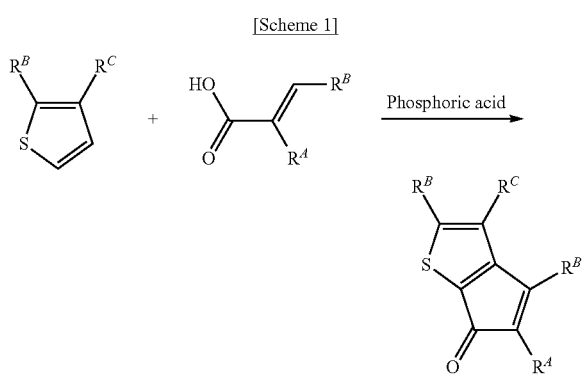

On the other hand, a variety of known methods can be employed to synthesize the transition metal compound of the formula 1 from the precursor for transition metal compound represented by the formula 2 obtained by the above-stated preparation method. According to one embodiment of the present invention, 2 equivalents of alkyl lithium is added to the precursor for transition metal compound of the formula 2 to induce deprotonation for producing a dilithium compound of cyclopentadienyl anion and amide anion, and $(Q^1)(Q^2)MCl_2$ is then added to the dilithium compound to eliminate 2 equivalents of LiCl, thereby preparing the transition metal compound of the formula 1.

According to another embodiment of the present invention, the compound of the formula 2 is reacted with $M(NMe_2)_4$ to eliminate 2 equivalents of $HNME_2$ and produce a transition metal compound of the formula 1, where both $Q^1$ and $Q^2$ are $NMe_2$. The transition metal compound is then reacted with $Me_3SiCl$ or $Me_2SiCl_2$ to replace the $NMe_2$ ligand with a chlorine ligand.

On the other hand, the catalyst used in the preparation method of the present invention may further comprise a co-catalyst compound.

The co-catalyst compound is to activate the transition metal compound of the formula 1. Thus, any kind of compound can be used as the co-catalyst compound without limitation in its construction, provided that it can activate the transition metal compound without deteriorating the catalytic activity of the catalyst of the present invention.

In accordance with one embodiment of the present invention, the co-catalyst compound is preferably at least one selected from the group consisting of compounds represented by the following formula 6, 7, or 8:

—[Al($R^{61}$)—O]$_a$—      [Formula 6]

In the formula 6, $R^{61}$ is independently a halogen radical, a $C_1$-$C_{20}$ hydrocarbyl radical, or a halogen-substituted $C_1$-$C_{20}$ hydrocarbyl radical; and a is an integer of 2 or above.

D($R^{71}$)$_3$      [Formula 7]

In the formula 7, D is aluminum (Al) or boron (B); and $R^{71}$ is independently a halogen radical, a $C_1$-$C_{20}$ hydrocarbyl radical, or a halogen-substituted $C_1$-$C_{20}$ hydrocarbyl radical.

[L-H]$^+$[Z(A)$_4$]$^-$ or [L]$^+$[Z(A)$_4$]$^-$      [Formula 8]

In the formula 8, L is a neutral or cationic Lewis acid; Z is a Group 13 element; and A is independently a $C_6$-$C_{20}$ aryl or $C_1$-$C_{20}$ alkyl radical having at least one hydrogen atom substituted with a halogen radical, a $C_1$-$C_{20}$ hydrocarbyl radical, a $C_1$-$C_{20}$ alkoxy radical, or a $C_6$-$C_{20}$ aryloxy radical.

In this regard, the co-catalyst compound of the formula 6 is not specifically limited in its construction, provided that it is alkylaluminoxane, and may be preferably methylaluminoxane, ethylaluminoxane, butylaluminoxane, hexylaluminoxane, octylaluminoxane, decylaluminoxane, etc.

Further, the co-catalyst compound represented by the formula 7 may be trialkylaluminum (e.g., trimethylaluminum, triethylaluminum, tributylaluminum, trihexylaluminum, trioctylaluminum, tridecylaluminum, etc.); dialkylaluminum alkoxide (e.g., dimethylaluminum methoxide, diethylaluminum methoxide, dibutylaluminum methoxide, etc.); dialkylaluminum halide (e.g., dimethylaluminum chloride, diethylaluminum chloride, dibutylaluminum chloride, etc.); alkylaluminum dialkoxide (e.g., methylaluminum dimethoxide, ethylaluminum dimethoxide, butylaluminum dimethoxide, etc.); alkylaluminum dihalide (e.g., methylaluminum dichloride, ethylaluminum dichloride, butylaluminum dichloride, etc.); trialkyl boron (e.g., trimethyl boron, triethyl boron, triisobutyl boron, tripropyl boron, tributyl boron, etc.); or tris-pentafluorophenyl boron.

Further, the co-catalyst compound represented by the formula 8 may be trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentalluorophenyl)borate, tri(sec-butyl)ammonium tetrakis(pentafluorophenyl)borate, N,N-dimethylanilinium tetrakis(pentafluorophenyl)borate, N,N-dimethylanilinium n-butyl tris(pentafluorophenyl)borate, N,N-dimethylanilinium benzyl tris(pentafluorophenyl)borate, N,N-dimethylanilinium tetrakis(4-(t-butyldimethylsilyl)-2,3,5,6-tetrafluorophenyl)borate, N,N-dimethylanilinium tetrakis(4-(t-triisopropylsilyl)-2,3,5,6-tetrafluorophenyl)borate, N,N-dimethylanilinium pentafluorophenoxy tris(pentafluorphenyl)borate, N,N-diethylanilinium tetrakis(pentafluorphenyl)borate, N,N-dimethyl-2,4,6-trimethylanilinium tetrakis(pentafluorophenyl)borate, N,N-dimethylammonium tetrakis(2,3,5,6-tetrafluorophenyl)borate, N,N-diethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-dimethyl-2,4,6-trimethylanilinium tetrakis(2,3,4,6-tetrafluorophenyl)borate, and so forth Further, the co-catalyst compound of the formula 8 may also be dialkylammonium (e.g., di-(i-propyl)ammonium tetrakis(pentafluorophenyl)borate, dicyclohexylammonium tetrakis(pentafluorophenyl)borate, etc.); trialkylphosphonium (e.g., triphenylphosphonium tetrakis(pentafluorophenyl)borate, tri(o-tolyl)phosphonium tetrakis(pentafluorophenyl)borate, tri(2,6-dimethylphenyl)phosphonium tetrakis(pentafluorophenyl)borate, etc.); dialkyloxonium (e.g., diphenyloxonium tetrakis(pentafluorophenyl)borate, di(o-tolyl)oxonium tetrakis(pentafluororphenyl)borate, di(2,6-dimethylphenyloxonium tetrakis(pentafluorophenyl)borate, etc.); dialkylsulfonium (e.g., diphenylsulfonium tetrakis(pentafluorophenyl)borate, di(o-tolyl)sulfonium tetrakis(pentafluorophenyl)borate, bis(2,6-dimethylphenyl)sulfonium tetrakis(pentafluorophenyl)borate, etc.); or carbonium salts (e.g., tropylium tetrakis(pentafluorophenyl)borate, triphenylmethylcarbenium tetrakis(pentafluorophenyl)borate, benzene(diazonium)tetrakis(pentafluorophenyl)borate, etc.).

According to the present invention, in order for the co-catalyst compound to exhibit the enhanced effect of activation, the conditions are preferably given as follows: in the formula 6, $R^{61}$ is methyl, ethyl, n-butyl, or isobutyl; in the formula 7, D is aluminum (Al), and $R^{71}$ is methyl or isobutyl;

or D is boron (B), and $R^{71}$ is pentafluorophenyl; and in the formula 8, $[L-H]^+$ is a dimethylanilinium cation, $[Z(A)_4]^-$ is $[B(C_6F_5)_4]^-$, and $[L]^+$ is $[(C_6H_5)_3C]^+$.

The added amount of the co-catalyst compound may be determined in consideration of the added amount of the transition metal compound of the formula 1, the required amount of the co-catalyst for sufficient activation of the transition metal compound, and so forth.

According to the present invention, the content of the co-catalyst compound is given such that the molar ratio of a metal in the co-catalyst compound with respect to one mole of a transition metal in the transition metal compound of the formula 1 is 1:1 to 1:100,000, preferably 1:1 to 1:10,000, more preferably 1:1 to 1:5,000.

More specifically, the co-catalyst of the formula 6 may be used at a molar ratio of 1:1 to 1:100,000, preferably 1:5 to 1:50,000, more preferably 1:10 to 1:20,000 with respect to the transition metal compound of the formula 1.

Further, the co-catalyst compound of the formula 7, where D is boron (B), may be used at a molar ratio of 1:1 to 1:100, preferably 1:1 to 1:10, more preferably 1:1 to 1:3, with respect to the transition metal compound of the formula 1.

Although dependent upon the amount of water in the polymerization system, the co-catalyst compound of the formula 7, where D is aluminum (Al), may be used at a molar ratio of 1:1 to 1:1,000, preferably 1:1 to 1:500, more preferably 1:1 to 1:100, with respect to the transition metal compound of the formula 1.

Further, the co-catalyst of the formula 8 may be contained at a molar ratio of 1:1 to 1:100, preferably 1:1 to 1:10, more preferably 1:1 to 1:4 with respect to the transition metal compound of the formula 1.

On the other hand, the catalyst used in the preparation method of the present invention may be a catalyst in which the transition metal compound of the formula 1 or a combination of the transition metal compound and the co-catalyst compound is bound to the surface of a support.

In this regard, the support as used herein may be any kind of inorganic or organic support used in the preparation of a catalyst in the prior art.

According to one embodiment of the present invention, the support may be $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2$—$TiO_2$—MgO, bauxite, zeolite, starch, cyclodextrine, or synthetic polymer.

Preferably, the support includes hydroxyl groups on its surface and may be at least one selected from the group consisting of silica, silica-alumina, and silica-magnesia.

The supporting method for the transition metal compound and the co-catalyst compound on a support may include: a method of directly supporting the transition metal compound on a dehydrated support; a method of pre-treating the support with the co-catalyst compound and then adding the transition metal compound; a method of supporting the transition metal compound on a support and then adding the co-catalyst compound for after-treatment of the support; or a method of reacting the transition metal compound and the co-catalyst compound and then adding the support.

In accordance with one embodiment of the present invention, the solvent as used in the supporting method is, for example, aliphatic hydrocarbon-based solvents (e.g., pentane, hexane, heptane, octane, nonane, decane, undecane, dodecane, etc.); aromatic hydrocarbon-based solvents (e.g., benzene, monochlorobenzene, dichlorobenzene, trichlorobenzene, toluene, etc.); halogenated aliphatic hydrocarbon-based solvents (e.g., dichloromethane, trichloromethane, dichloroethane, trichloroethane, etc.); or mixtures thereof.

In terms of the efficiency of the process for supporting the transition metal compound and the co-catalyst compound on a support, the supporting process may be preferably carried out at a temperature of −70 to 200° C., preferably −50 to 150° C., more preferably 0 to 100° C.

The preparation method for polypropylene according to the present invention may comprise polymerizing a propylene monomer in the presence of the afore-mentioned catalyst.

In this regard, the propylene monomer is not specifically limited and may include any kind of propylene generally used in the related art of the present invention.

Further, the polymerization step may be carried out by way of slurry, solution, gas, or bulk polymerization.

In the polymerization step conducted in the solution or slurry phase, the solvent or the olefin-based monomer itself can be used as a medium.

The solvent as used in the polymerization step may be aliphatic hydrocarbon solvents (e.g., butane, isobutane, pentane, hexane, heptane, octane, nonane, decane, undecane, dodecane, cyclopentane, methylcyclopentane, cyclohexane, etc.); aromatic hydrocarbon-based solvents (e.g., benzene, monochlorobenzene, dichlorobenzene, trichlorobenzene, toluene, xylene, chlorobenzene, etc.); halogenated aliphatic hydrocarbon solvents (e.g., dichloromethane, trichloromethane, chloroethane, dichloroethane, trichloroethane, 1,2-dichloroethane, etc.); or mixtures thereof.

In the polymerization step, the added amount of the catalyst is not specifically limited and may be determined within a range allowing a sufficient polymerization reaction of the monomer depending on whether the process is carried out by way of slurry, solution, gas, or bulk polymerization.

According to the present invention, the added amount of the catalyst is $10^{-8}$ to 1 mol/L, preferably $10^{-7}$ to $10^{-1}$ mol/L, more preferably $10^{-7}$ to $10^{-2}$ mol/L, based on the concentration of the central metal of the transition metal compound per unit volume (L) of the monomer.

Further, the polymerization step may be carried out by way of the batch type, semi-continuous type, or continuous type reaction.

The temperature and pressure conditions for the polymerization step are not specifically limited and may be determined in consideration of the efficiency of the polymerization reaction depending on the types of the reaction and the reactor used.

According to the present invention, the polymerization step may be carried out at a temperature of −50 to 500° C., preferably 0 to 400° C., more preferably 0 to 300° C. Further, the polymerization step may be carried out under the pressure of 1 to 3,000 atm, preferably 1 to 1,000 atm, more preferably 1 to 500 atm.

On the other hand, the preparation method for polypropylene according to the present invention allows it to control the fine-structure characteristics of the copolymer with ease by using the afore-mentioned catalyst, thereby providing a polypropylene with high molecular weight and low density.

In other words, the polypropylene may have a weight average molecular weight (Mw) of 20,000 to 1,000,000, preferably 50,000 to 900,000, more preferably 50,000 to 800,000.

The polypropylene may have a density of 0.8 to 0.9 g/ml, preferably 0.82 to 0.9 g/ml, more preferably 0.82 to 0.89 g/ml.

Further, the polypropylene may have an isotacticity (Pentad I.I, mmmm) of 5 to 20%, preferably 5 to 18%, more preferably 5 to 15%.

Further, the polypropylene may have a molecular weight distribution (Mw/Mn) of 1 to 10, preferably 1.5 to 8, more preferably 2 to 6.

On the other hand, the preparation method for copolymer according to the present invention may further comprise, in addition to the afore-mentioned steps, a step known to those skilled in the art before or after the afore-mentioned steps, which are not given to limit the preparation method of the present invention.

Hereinafter, a detailed description will be given as to the present invention in accordance with the preferred embodiments, which are given by way of illustration only and not intended to limit the scope of the present invention.

The following synthesis procedures (i) and (ii) for the precursor and the transition metal compound were performed in the atmosphere of inert gas, such as nitrogen or argon, according to the following Schemes 2 and 3, using the standard Schlenk and glove box techniques.

The individual compounds in the Scheme 2 come in different substituents. The substituents are presented in the table given below the corresponding compound (for example, the compound D-2 denotes a compound having a hydrogen atom for $R^a$ and a methyl group for $R^b$ and $R^c$).

In the Scheme 2, the compound C(C-1, C-2, or C-3) was synthesized by a known method (*J. Organomet. Chem.*, 2005, 690, 4213).

[Scheme 2]

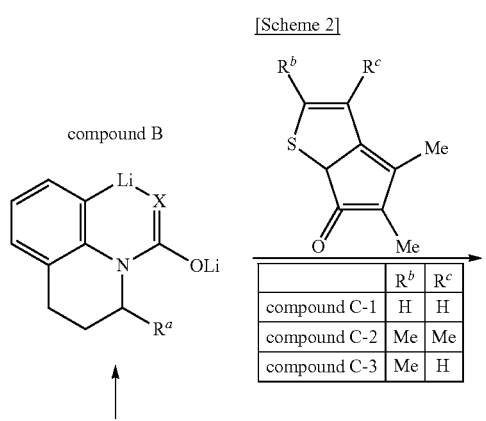

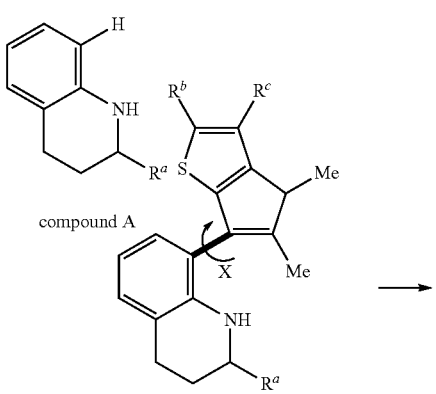

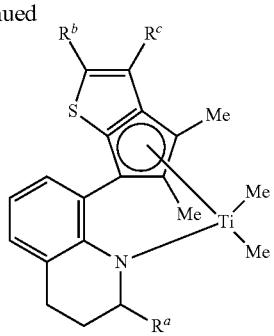

| | $R^a$ | $R^b$ | $R^c$ |
|---|---|---|---|
| compound E-1 | H | H | H |
| compound E-2 | H | Me | Me |
| compound E-3 | Me | H | H |
| compound E-4 | Me | Me | Me |
| compound E-5 | Me | H | Me |

(i) Synthesis of Precursor

Example i-1

Synthesis of Precursor D-1

A Schlenk flask containing 1,2,3,4-tetrahydroquinoline (1.00 g, 7.51 mmol) and diethyl ether (16 ml) was cooled down in a cold bath at −78° C. and stirred while n-butyl lithium (3.0 mL, 7.5 mmol, 2.5 M hexane solution) was slowly added under the nitrogen atmosphere. After one-hour agitation at −78° C., the flask was gradually warmed up to the room temperature. A light yellowish solid precipitated, and the butane gas was removed through a bubbler. The flask was cooled down back to −78° C. and supplied with carbon dioxide. Upon injection of carbon dioxide, the slurry-type solution turned to a clear homogenous solution. After one-hour agitation at −78° C., the flask was gradually warmed up −20° C. while the extra carbon dioxide was removed through the bubbler to remain a white solid as a precipitate.

Tetrahydrofuran (0.60 g, 8.3 mmol) and t-butyl lithium (4.9 mL, 8.3 mmol, 1.7 M pentane solution) were sequentially added at −20° C. in the nitrogen atmosphere, and the flask was agitated for about 2 hours. Subsequently, a tetrahydrofuran solution (19 mL) containing lithium chloride and the compound C-1 (1.06 g, 6.38 mmol) was added in the nitrogen atmosphere. The flask was agitated at −20° C. for one hour and then gradually warmed up to the room temperature. After one-hour agitation at the room temperature, water (15 mL) was added to terminate the reaction. The solution was moved to a separatory funnel to extract the organic phase. The extracted organic phase was put in a separatory funnel, and then hydrochloric acid (2 N, 40 mL) was added. After shaking up the solution for about 2 minutes, an aqueous solution of sodium hydrocarbonate (60 mL) was slowly added to neutralize the solution. The organic phase was separated and removed of water with anhydrous magnesium sulfate to eliminate the solvent and yield a sticky product. The product thus obtained was purified by the silica gel column chromatography using a mixed solvent of hexane and ethylacetate (v/v, 50:1) to yield 77.2 mg of the desired compound (43% yield).

In the $^1$H NMR spectrum of the final product, there was observed a set of two signals at ratio of 1:1, resulting from the difficulty of rotating about the carbon-carbon bond (marked as a thick line in the Scheme 2) between phenylene and cyclopentadiene. In the following $^{13}$C NMR spectrum, the values in parenthesis are chemical shift values split due to the difficulty of rotation.

$^1$H NMR (C$_6$D$_6$): δ 7.22 and 7.17 (br d, J=7.2 Hz, 1H), 6.88 (s, 2H), 6.93 (d, J=7.2 Hz, 1H), 6.73 (br t, J=7.2 Hz, 1H), 3.84 and 3.80 (s, 1H, NH), 3.09 and 2.98 (q, J=8.0 Hz, 1H, CHMe), 2.90-2.75 (br, 2H, CH$_2$), 2.65-2.55 (br, 2H, CH$_2$), 1.87 (s, 3H, CH$_3$), 1.70-1.50 (m, 2H, CH$_2$), 1.16 (d, J=8.0 Hz, 3H, CH$_3$) ppm.

$^{13}$C NMR (C$_6$D$_6$): 151.64 (151.60), 147.74 (147.61), 146.68, 143.06, 132.60, 132.30, 129.85, 125.02, 121.85, 121.72, 119.74, 116.87, 45.86, 42.54, 28.39, 22.89, 16.32, 14.21 ppm.

Example i-2

Synthesis of Precursor D-2

The procedures were performed in the same manner as described in the synthesis of the compound D-1 in Example i-1, excepting that the compound C-2 was used rather than the compound C-1, to yield a precursor compound D-2. The yield was 53%.

In the $^1$H NMR spectrum of the final product, there was observed a set of two signals at ratio of 1:1, resulting from the difficulty of rotating about the carbon-carbon bond (marked as a thick line in the Scheme 2) between phenylene and cyclopentadiene.

$^1$H NMR (C$_6$D$_6$): δ 7.23 (d, J=7.2 Hz, 1H), 6.93 (d, J=7.2 Hz, 1H), 6.74 (br t, J=7.2 Hz, 1H), 4.00 and 3.93 (s, 1H, NH), 3.05 (br q, J=8.0 Hz, 1H, CHMe), 3.00-2.80 (br, 2H, CH$_2$), 2.70-2.50 (br, 2H, CH$_2$), 2.16 (s, 3H, CH$_3$), 2.04 (br s, 3H, CH$_3$), 1.91 (s, 3H, CH$_3$), 1.75-1.50 (m, 2H, CH$_2$), 1.21 (d, J=8.0 Hz, 3H, CH$_3$) ppm.

$^{13}$C NMR (C$_6$D$_6$): 151.60 (151.43), 145.56 (145.36), 143.08, 141.43, 132.90, 132.68, 132.43, 129.70, 121.63, 120.01, 116.77, 46.13, 42.58, 28.42, 22.97, 15.06, 14.19, 14.08, 12.70 ppm.

Example i-3

Synthesis of Precursor D-3

The procedures were performed in the same manner as described in the synthesis of the compound D-1 in Example i-1, excepting that tetrahydroquinaldine was used rather than tetrahydroquinoline, to yield a precursor compound D-3. The yield was 63%.

In the $^1$H NMR spectrum of the final product, a certain signal was split into a set of four signals at ratio of 1:1:1:1, resulting from the difficulty of rotating about the carbon-carbon bond (marked as a thick line in the Scheme 2) between phenylene and cyclopentadiene and isomerism pertaining to the existence of two chiral centers.

$^1$H NMR (C$_6$D$_6$): δ 7.33, 7.29, 7.22, and 7.17 (d, J=7.2 Hz, 1H), 6.97 (d, J=7.2 Hz, 1H), 6.88 (s, 2H), 6.80-6.70 (m, 1H), 3.93 and 3.86 (s, 1H, NH), 3.20-2.90 (m, 2H, NCHMe, CHMe), 2.90-2.50 (m, 2H, CH$_2$), 1.91, 1.89, and 1.86 (s, 3H, CH$_3$), 1.67-1.50 (m, 1H, CH$_2$), 1.50-1.33 (m, 1H, CH$_2$), 1.18, 1.16, and 1.14 (s, 3H, CH$_3$), 0.86, 0.85, and 0.80 (d, J=8.0 Hz, 3H, CH$_3$) ppm.

$^{13}$C NMR (C$_6$D$_6$): 151.67, 147.68 (147.56, 147.38), 147.06 (146.83, 146.28, 146.10), 143.01 (142.88), 132.99 (132.59), 132.36 (131.92), 129.69, 125.26 (125.08, 124.92, 124.83), 122.03, 121.69 (121.60, 121.28), 119.74 (119.68, 119.46), 117.13 (117.07, 116.79, 116.72), 47.90 (47.73), 46.04 (45.85), 31.00 (30.92, 30.50), 28.00 (27.83, 27.64), 23.25 (23.00), 16.38 (16.30), 14.63 (14.52, 14.18) ppm.

Example i-4

Synthesis of Precursor D-4

The procedures were performed in the same manner as described in the synthesis of the compound D-1 in Example i-1, excepting that the compound C-2 and tetrahydroquinaldine were used rather than the compound C-1 and tetrahydroquinoline, to yield a precursor compound D-4. The yield was 63%.

In the $^1$H NMR spectrum of the final product, a certain signal was split into a set of four signals at ratio of 1:1:1:1, resulting from the difficulty of rotating about the carbon-carbon bond (marked as a thick line in the Scheme 2) between phenylene and cyclopentadiene and isomerism pertaining to the existence of two chiral centers.

$^1$H NMR (C$_6$D$_6$): δ 7.32, 7.30, 7.22, and 7.19 (d, J=7.2 Hz, 1H), 6.97 (d, J=7.2 Hz, 1H), 6.85-6.65 (m, 1H), 4.10-3.90 (s, 1H, NH), 3.30-2.85 (m, 2H, NCHMe, CHMe), 2.85-2.50 (m, 2H, CH$_2$), 2.15 (s, 3H, CH$_3$), 2.02 (s, 3H, CH$_3$), 1.94, 1.92, and 1.91 (s, 3H, CH$_3$), 1.65-1.50 (m, 1H, CH$_2$), 1.50-1.33 (m, 1H, CH$_2$), 1.22, 1.21, 1.20, and 1.19 (s, 3H, CH$_3$), 1.10-0.75 (m, 3H, CH$_3$) ppm.

$^{13}$C NMR (C$_6$D$_6$): 151.67 (151.57), 145.58 (145.33, 145.20), 143.10 (143.00, 142.89), 141.62 (141.12), 134.08 (133.04), 132.84 (132.70, 136.60), 132.50 (132.08), 129.54, 121.52 (121.16), 119.96 (119.71), 117.04 (116.71), 47.90 (47.78), 46.29 (46.10), 31.05 (30.53), 28.02 (28.67), 23.37 (23.07), 15.22 (15.04), 14.87 (14.02, 14.21), 12.72 (12.67) ppm.

Example i-5

Synthesis of Precursor D-5

The procedures were performed in the same manner as described in the synthesis of the compound D-1 in Example i-1, excepting that the compound C-3 and tetrahydroquinaldine were used rather than the compound C-1 and tetrahydroquinoline, to yield a precursor compound D-5. The yield was 48%.

In the $^1$H NMR spectrum of the final product, a certain signal was split into a set of four signals at ratio of 1:1:1:1, resulting from the difficulty of rotating about the carbon-carbon bond (marked as a thick line in the Scheme 2) between phenylene and cyclopentadiene and isomerism pertaining to the existence of two chiral centers.

$^1$H NMR (C$_6$D$_6$): δ 7.32, 7.29, 7.22 and 7.18 (d, J=7.2 Hz, 1H), 6.96 (d, J=7.2 Hz, 1H), 6.84-6.68 (m, 1H), 6.60 (d, J=7.2 Hz, 1H), 4.00-3.92 (s, 1H, NH), 3.30-2.90 (m, 2H, NCHMe, CHMe), 2.90-2.55 (m, 2H, CH$_2$), 2.27 (s, 3H, CH$_3$), 1.94, 1.91 and 1.89 (s, 3H, CH$_3$), 1.65-1.54 (m, 1H, CH$_2$), 1.54-1.38 (m, 1H, CH$_2$), 1.23, 1.22, and 1.20 (s, 3H, CH$_3$), 1.00-0.75 (m, 3H, CH$_3$) ppm.

$^{13}$C NMR (C$_6$D$_6$): 151.51, 145.80, 145.64, 145.45, 144.40, 144.22, 143.76, 143.03, 142.91, 139.78, 139.69, 139.52, 133.12, 132.74, 132.52, 132.11, 129.59, 121.52, 121.19, 120.75, 120.47, 119.87, 119.69, 116.99, 116.76, 47.90, 47.77, 46.43, 46.23, 32.55, 30.98, 30.51, 27.95, 27.67, 23.67, 23.31, 23.06, 16.52, 15.01, 14.44, 14.05 ppm.

(ii) Synthesis of Transition Metal Compound

Example ii-1

Synthesis of Transition Metal Compound E-1

In a dry box, the compound D-1 (0.10 g, 0.36 mmol) synthesized in Example i-1 and dimethyl ether were put into a round-bottomed flask and cooled down to −30° C. N-butyl lithium (2.5 M hexane solution, 0.2 g, 0.71 mmol) was gradually added to the flask under agitation to activate the reaction at −30° C. for 2 hours. Warmed up to the room temperature, the flask was agitated for more 3 hours for the reaction. After cooled down back to −30° C., to the flask were added methyl lithium (1.6 M diethyl ether solution, 0.33 g, 0.71 mmol) and then TiCl$_4$.DME (DME: dimethoxyethane, 0.10 g, 0.36 mmol). The flask, while warmed up to the room temperature, was agitated for 3 hours and then removed of the solvent using a vacuum line. Pentane was used to extract the compound. The removal of the solvent produced 0.085 g of the final compound as a brownish powder (60% yield).

$^1$H NMR (C$_6$D$_6$): δ 7.09 (d, J=7.2 Hz, 1H), 6.91 (d, J=7.2 Hz, 1H), 6.81 (t, J=7.2 Hz, 1H), 6.74 (s, 2H), 4.55 (dt, J=14, 5.2 Hz, 1H, NCH$_2$), 4.38 (dt, J=14, 5.2 Hz, 1H, NCH$_2$), 2.50-2.30 (m, 2H, CH$_2$), 2.20 (s, 3H), 1.68 (s, 3H), 1.68 (quintet, J=5.2 Hz, CH$_2$), 0.72 (s, 3H, TiMe), 0.38 (s, 3H, TiMe) ppm.

$^{13}$C{$^1$H} NMR (C$_6$D$_6$): 161.46, 142.43, 140.10, 133.03, 130.41, 129.78, 127.57, 127.34, 121.37, 120.54, 120.51, 120.34, 112.52, 58.50, 53.73, 49.11, 27.59, 23.27, 13.19, 13.14 ppm.

Example ii-2

Synthesis of Transition Metal Compound E-2

The procedures were performed in the same manner as described in the synthesis of the compound E-1 in Example ii-1, excepting that the compound D-2 was used rather than the compound D-1, to yield a transition metal compound E-2. The yield was 53%.

$^1$H NMR (C$_6$D$_6$): δ 7.10 (d, J=7.2 Hz, 1H), 6.91 (d, J=7.2 Hz, 1H), 6.81 (t, J=7.2 Hz, 1H), 4.58 (dt, J=14, 5.2 Hz, 1H, NCH$_2$), 4.42 (dt, J=14, 5.2 Hz, 1H, NCH$_2$), 2.50-2.38 (m, 2H, CH$_2$), 2.32 (s, 3H), 2.11 (s, 3H), 2.00 (s, 3H), 1.71 (s, 3H), 1.67 (quintet, J=5.2 Hz, CH$_2$), 0.72 (s, 3H, TiMe), 0.38 (s, 3H, TiMe) ppm.

$^{13}$C{$^1$H} NMR(C$_6$D$_6$): 161.58, 141.36, 138.41, 137.20, 132.96, 129.70, 127.53, 127.39, 126.87, 121.48, 120.37, 120.30, 113.23, 56.50, 53.13, 49.03, 27.64, 23.34, 14.21, 13.40, 12.99, 12.94 ppm. Anal. Calc. (C$_{22}$H$_{27}$NSTi): C, 68.56; H, 7.06; N, 3.63. Found: C, 68.35H, 7.37 N, 3.34%.

Example ii-3

Synthesis of Transition Metal Compound E-3

The procedures were performed in the same manner as described in the synthesis of the compound E-1 in Example ii-1, excepting that the compound D-3 was used rather than the compound D-1, to yield a transition metal compound E-3. The yield was 51%. The final product was identified as a 1:1 mixture (the direction of the thiophene cyclic radical to the direction of the methyl radical on tetrahydroquinoline).

$^1$H NMR (C$_6$D$_6$): δ 7.11 and 7.08 (d, J=7.2 Hz, 1H), 6.96 and 6.95 (d, J=7.2 Hz, 1H), 6.82 and 6.81 (t, J=7.2 Hz, 1H), 6.77 and 6.76 (d, J=7.2 Hz, 1H), 6.74 and 6.73 (d, J=7.2 Hz, 1H), 5.42 (m, 1H, NCH), 2.75-2.60 (m, 1H, CH$_2$), 2.45-2.25 (m, 1H, CH$_2$), 2.24 and 2.18 (s, 3H), 1.73 and 1.63 (s, 3H), 1.85-1.50 (m, 2H, CH$_2$), 1.17 and 1.15 (d, J=4.8 Hz, 3H), 0.76 and 0.70 (s, 3H, TiMe), 0.42 and 0.32 (s, 3H, TiMe) ppm.

$^{13}$C{$^1$H} NMR (C$_6$D$_6$): 159.58, 159.28, 141.88, 141.00, 139.63, 138.98, 134.45, 130.85, 130.50, 129.59, 129.50, 129.47, 127.23, 127.20, 127.17, 127.11, 120.77, 120.70, 120.40, 120.00, 119.96, 119.91, 118.76, 118.57, 113.90, 110.48, 59.61, 56.42, 55.75, 51.96, 50.11, 49.98, 27.41, 27.11, 21.89, 20.09, 19.67, 12.94, 12.91, 12.65 ppm.

Example ii-4

Synthesis of Transition Metal Compound E-4

The procedures were performed in the same manner as described in the synthesis of the compound E-1 in Example ii-1, excepting that the compound D-4 was used rather than the compound D-1, to yield a transition metal compound E-4. The yield was 57%. The final product was identified as a 1:1 mixture (the direction of the thiophene cyclic radical to the direction of the methyl radical on tetrahydroquinoline).

$^1$HNMR (C$_6$D$_6$): δ 7.12 and 7.10 (d, J=7.2 Hz, 1H), 6.96 and 6.94 (d, J=7.2 Hz, 1H), 6.82 and 6.81 (t, J=7.2 Hz, 1H), 5.45 (m, 1H, NCH), 2.75-2.60 (m, 1H, CH$_2$), 2.45-2.20 (m, 1H, CH$_2$), 2.34 and 2.30 (s, 3H), 2.10 (s, 3H), 1.97 (s, 3H), 1.75 and 1.66 (s, 3H), 1.85-1.50 (m, 2H, CH$_2$), 1.20 (d, J=6.8 Hz, 3H), 0.76 and 0.72 (s, 3H, TiMe), 0.44 and 0.35 (s, 3H, TiMe) ppm.

$^{13}$C{$^1$H} NMR (C$_6$D$_6$): 160.13, 159.86, 141.33, 140.46, 138.39, 137.67, 136.74, 134.83, 131.48, 129.90, 129.78, 127.69, 127.65, 127.60, 127.45, 126.87, 126.81, 121.34, 121.23, 120.21, 120.15, 119.15, 118.93, 114.77, 111.60, 57.54, 55.55, 55.23, 51.73, 50.43, 50.36, 27.83, 27.67, 22.37, 22.31, 20.53, 20.26, 14.29, 13.51, 13.42, 13.06, 12.80 ppm.

Example ii-5

Synthesis of Transition Metal Compound E-5

The procedures were performed in the same manner as described in the synthesis of the compound E-1 in Example ii-1, excepting that the compound D-5 was used rather than the compound D-1, to yield a transition metal compound E-5. The yield was 57%. The final product was identified as a 1:1 mixture (the direction of the thiophene cyclic radical to the direction of the methyl radical on tetrahydroquinoline).

$^1$H NMR (C$_6$D$_6$): δ 7.12 and 7.09 (d, J=7.2 Hz, 1H), 6.96 and 6.94 (d, J=7.2 Hz, 1H), 6.82 and 6.80 (t, J=7.2 Hz, 1H), 6.47 and 6.46 (d, J=7.2 Hz, 1H), 6.45 and 6.44 (d, J=7.2 Hz, 1H), 5.44 (m, 1H, NCH), 2.76-2.60 (m, 1H, CH$_2$), 2.44-2.18 (m, 1H, CH$_2$), 2.28 and 2.22 (s, 3H), 2.09 (s, 3H), 1.74 and 1.65 (s, 3H), 1.88-1.48 (m, 2H, CH$_2$), 1.20 and 1.18 (d, J=7.2 Hz, 3H), 0.77 and 0.71 (s, 3H, TiMe), 0.49 and 0.40 (s, 3H, TiMe) ppm.

$^{13}$C{$^1$H} NMR (C$_6$D$_6$): 159.83, 159.52, 145.93, 144.90, 140.78, 139.93, 139.21, 138.86, 135.26, 131.56, 129.69, 129.57, 127.50, 127.46, 127.38, 127.24, 121.29, 121.16, 120.05, 119.96, 118.90, 118.74, 117.99, 117.74, 113.87, 110.38, 57.91, 55.31, 54.87, 51.68, 50.27, 50.12, 34.77, 27.58, 27.27, 23.10, 22.05, 20.31, 19.90, 16.66, 14.70, 13.11, 12.98, 12.68 ppm.

Example ii-6

Synthesis of Transition Metal Compound E-6

The transition metal compound E-6 was synthesized according to the following Scheme 3.

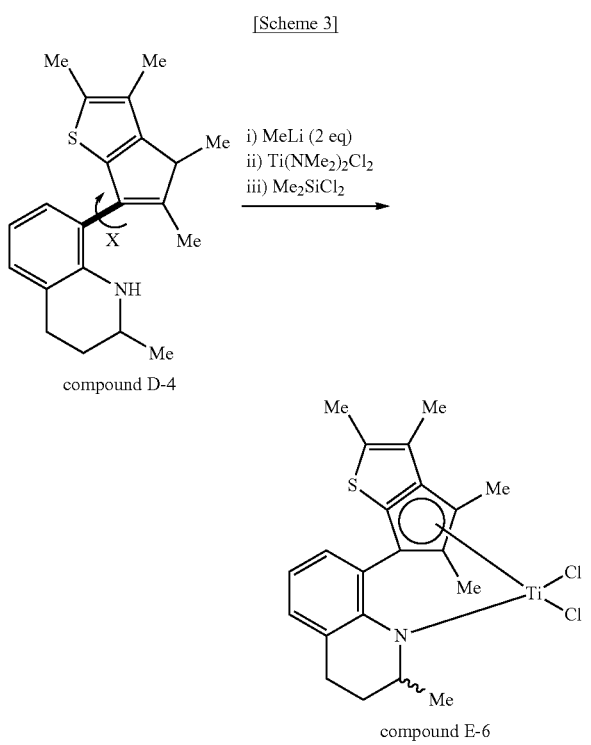

Methyl lithium (1.63 g, 3.55 mmol, 1.6 M diethyl ether solution) was added dropwise to a diethyl ether solution (10 mL) containing the compound D-4 (0.58 g, 1.79 mmol). The solution was agitated overnight at the room temperature and cooled down to −30° C. Then, Ti(NMe$_2$)$_2$Cl$_2$ (0.37 g, 1.79 mmol) was added at once. After 3-hour agitation, the solution was removed of all the solvent with a vacuum pump. The solid thus obtained was dissolved in toluene (8 mL), and Me$_2$SiCl$_2$ (1.16 g, 8.96 mmol) was added to the solution. The solution was agitated at 80° C. for 3 days and removed of the solvent with a vacuum pump to obtain a reddish solid compound (0.59 g, 75% yield). The $^1$H NMR spectrum showed the existence of two stereo-structural compounds at ratio of 2:1.

$^1$H NMR (C$_6$D$_6$): δ 7.10 (t, J=4.4 Hz, 1H), 6.90 (d, J=4.4 Hz, 2H), 5.27 and 5.22 (m, 1H, NCH), 2.54-2.38 (m, 1H, CH$_2$), 2.20-2.08 (m, 1H, CH$_2$), 2.36 and 2.35 (s, 3H), 2.05 and 2.03 (s, 3H), 1.94 and 1.93 (s, 3H), 1.89 and 1.84 (s, 3H), 1.72-1.58 (m, 2H, CH$_2$), 1.36-1.28 (m, 2H, CH$_2$), 1.17 and 1.14 (d, J=6.4, 3H, CH$_3$) ppm.

$^{13}$C{$^1$H} NMR (C$_6$D$_6$): 162.78, 147.91, 142.45, 142.03, 136.91, 131.12, 130.70, 130.10, 128.90, 127.17, 123.39, 121.33, 119.87, 54.18, 26.48, 21.74, 17.28, 14.46, 14.28, 13.80, 13.27 ppm.

(iii) Preparation of Polypropylene

The individual polymerization reaction was carried out in an airtight autoclave using required amounts of a solvent, a co-catalyst compound, and monomers, and then a transition metal compound.

After completion of the polymerization, the polymer product was measured in regard to the molecular weight and the molecular weight distribution by the GPC (Gel Permeation Chromatography) (instrument: PL-GPC220 supplied by Agilent), and the melting point by the DSC (Differential Scanning calorimetry) (instrument: Q200 supplied by TA Instruments).

The isotacticity (Pentad, I.I, mmmm) of the polypropylene was analyzed by $^{13}$C NMR (Avance 400 Spectrometer supplied by Bruker) at 100° C. using the polypropylene product dissolved in trichlorobenzene and benzene-d$_6$ (C$_6$D$_6$). The measurement results are presented in Table 1.

Example iii-1

An autoclave (capacity: 2 L, stainless steel) was purged with nitrogen at the room temperature and filled with about 40 ml of a toluene solution (containing 10 wt. % of methylaluminoxane in toluene, 6 mmol of Al, as supplied by Albemarle). Then, 500 g of propylene was added, and the resultant solution was warmed up to 70° C. Subsequently, a solution (1.5 ml, 3.0 μmol of Ti) of the transition metal compound E-6 of Example ii-6 dissolved in toluene was added to the autoclave and then subjected to polymerization reaction for one hour.

After completion of the polymerization reaction, the resultant solution was cooled down to the room temperature and removed of the extra propylene. The polymer product thus obtained was collected and dried in a vacuum oven at 80° C. for at least 4 hours to yield polypropylene (137.9 g).

Example iii-2

An autoclave (capacity: 2 L, stainless steel) was purged with nitrogen at the room temperature and filled with 900 ml of n-hexane. Then, about 13.3 ml of a toluene solution (containing 10 wt. % of methylaluminoxane in toluene, 20 mmol of Al, as supplied by Albemarle) and 100 g of propylene were added in sequence. The resultant solution was warmed up to 70° C. Subsequently, a solution (5 ml, 10.0 μmol of Ti) of the transition metal compound E-6 of Example ii-6 dissolved in toluene was added to the autoclave and then subjected to polymerization reaction for one hour.

After completion of the polymerization reaction, the resultant solution was cooled down to the room temperature and removed of the extra propylene. The polymer product thus obtained was collected and dried in a vacuum oven at 80° C. for at least 4 hours to yield polypropylene (55.5 g).

Example iii-3

The procedures were performed in the same manner as described in Example iii-2, excepting that the polymerization reaction was carried out at 180° C. for 15 minutes to yield polypropylene (35.6 g).

Comparative Example iii-1

The procedures were performed in the same manner as described in Example iii-1, excepting that bisindenylzirconium dichloride (Ind$_2$ZrCl$_2$, supplied by Strem) was used as a catalyst rather than the transition metal compound E-6 of Example ii-6, to yield polypropylene (40 g).

Comparative Example iii-2

The procedures were performed in the same manner as described in Example iii-1, excepting that racemic ethylenebisindenylzirconium dichloride (supplied by Strem) was used as a catalyst rather than the transition metal compound E-6 of Example ii-6, to yield polypropylene (80 g).

TABLE 1

|  | Example iii-1 | Example iii-2 | Example iii-3 | Comparative Example iii-1 | Comparative Example iii-2 |
|---|---|---|---|---|---|
| Catalytic activity (kg-PP)/(mmol-Ti)(hour) | 46.0 | 5.55 | 14.2 | 13.3 | 26.7 |
| Mw (×10³) | 349 | 186 | 102 | 5.2 | 30.3 |
| Molecular weight distribution (Mw/Mn) | 5.25 | 3.02 | 4.01 | 2.65 | 2.63 |
| Melting point (° C.) | N/A | N/A | N/A | N/A | 130.6 |
| I.I. (%, mmmm) | 9.6 | 7.7 | 6.4 | 7.2 | 78.2 |
| Density (g/ml) | 0.850 | 0.864 | 0.860 | N.O. | N.O. |

(Note:
N.O. - Impossible to measure the property for the polymer with difficulty of preparing a press specimen due to the characteristic of the property.)

As can be seen from Table 1, a polypropylene with higher molecular weight and no melting point was obtained when polymerizing a propylene monomer using the catalyst of the present invention as in Examples iii-1, iii-2, and iii-3, rather than using the conventional transition metal compound as in Comparative Example iii-1 and iii-2.

The invention claimed is:

1. A method for preparing a polypropylene, comprising:
polymerizing a propylene monomer in the presence of a catalyst comprising a transition metal compound represented by the following formula 1:

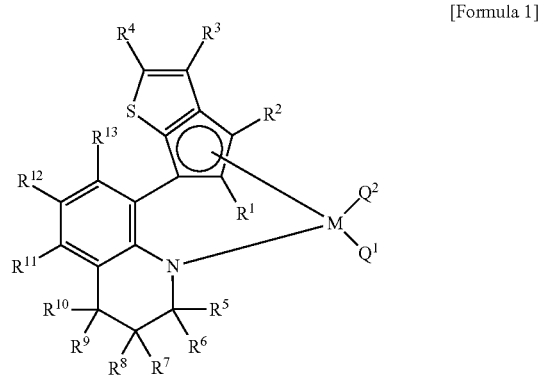

[Formula 1]

wherein M is a Group 4 transition metal;
$Q^1$ and $Q^2$ are independently a halogen, $C_1$-$C_{20}$ alkyl, $C_2$-$C_{20}$ alkenyl, $C_2$-$C_{20}$ alkynyl, $C_6$-$C_{20}$ aryl, $C_1$-$C_{20}$ alkyl $C_6$-$C_{20}$ aryl, $C_6$-$C_{20}$ aryl $C_1$-$C_{20}$ alkyl, $C_1$-$C_{20}$ alkylamido, $C_6$-$C_{20}$ arylamido, or $C_1$-$C_{20}$ alkylidene;
$R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, wherein $R^1$ and $R^2$ can be linked to each other to form a ring; $R^3$ and $R^4$ can be linked to each other to form a ring; and at least two of $R^5$ to $R^{10}$ can be linked to each other to form a ring; and
$R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, wherein $R^{11}$ and $R^{12}$, or $R^{12}$ and $R^{13}$ can be linked to each other to form a ring.

2. The method as claimed in claim 1, wherein M is titanium (Ti), zirconium (Zr), or hafnium (Hf);
$Q^1$ and $Q^2$ are independently methyl or chlorine;
$R^1$, $R^2$, $R^3$, $R^4$, and $R^5$ are independently hydrogen or methyl; and
$R^6$, $R^7$, $R^8$, $R^9$, $R^{10}$, $R^{11}$, $R^{12}$, and $R^{13}$ are independently hydrogen.

3. The method as claimed in claim 2, wherein at least one of $R^3$ and $R^4$ is methyl; and $R^5$ is methyl.

4. The method as claimed in claim 1, wherein the catalyst further comprises at least one co-catalyst compound selected from the group consisting of compounds represented by the following formula 6, 7, or 8:

—[Al($R^{61}$)—O]$_a$—  [Formula 6]

wherein $R^{61}$ is independently a halogen radical, a $C_1$-$C_{20}$ hydrocarbyl radical, or a halogen-substituted $C_1$-$C_{20}$ hydrocarbyl radical; and
a is an integer of 2 or above,

D($R^{71}$)$_3$  [Formula 7]

wherein D is aluminum (Al) or boron (B); and $R^{71}$ is independently a halogen radical, a $C_1$-$C_{20}$ hydrocarbyl radical, or a halogen-substituted $C_1$-$C_{20}$ hydrocarbyl radical,

[L-H]$^+$[Z(A)$_4$]$^-$ or [L]$^+$[Z(A)$_4$]$^-$  [Formula 8]

wherein L is a neutral or cationic Lewis acid;
Z is a Group 13 element; and
A is independently a $C_6$-$C_{20}$ aryl or $C_1$-$C_{20}$ alkyl radical having at least one hydrogen atom substituted with a halogen radical, a $C_1$-$C_{20}$ hydrocarbyl radical, a $C_1$-$C_{20}$ alkoxy radical, or a $C_6$-$C_{20}$ aryloxy radical.

5. The method as claimed in claim 4, wherein in the formula 6, $R^{61}$ is methyl, ethyl, n-butyl, or isobutyl;
in the formula 7, D is aluminum, and $R^{71}$ is methyl or isobutyl; or D is boron, and $R^{71}$ is pentafluorophenyl; and
in the formula 8, [L-H]$^+$ is a dimethylanilinium cation, [Z(A)$_4$]$^-$ is [B(C$_6$F$_5$)$_4$]$^-$, and [L]$^-$ is [(C$_6$H$_5$)$_3$C]$^+$.

6. The method as claimed in claim 4, wherein the content of the co-catalyst compound is given such that the molar ratio of a metal in the co-catalyst compound with respect to one mole of a transition metal in the transition metal compound of the formula 1 is 1:1 to 1:100,000.

7. The method as claimed in claim 1, wherein the catalyst comprises the transition metal compound of the formula 1 bound to at least one support selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2TiO_2$—MgO, bauxite, zeolite, starch, and cyclodextrine.

8. The method as claimed in claim 1, wherein the polymerization is carried out under conditions of −50 to 500° C. and 1 to 3,000 atm.

9. The method as claimed in claim 1, wherein the polypropylene has a weight average molecular weight of 20,000 to 1,000,000; and a density of 0.8 to 0.9 g/ml.

10. The method as claimed in claim 1, wherein the polypropylene has an isotacticity (Pentad I.I, mmmm) of 5 to 20%.

* * * * *

UNITED STATES PATENT AND TRADEMARK OFFICE
CERTIFICATE OF CORRECTION

PATENT NO. : 8,889,804 B2  
APPLICATION NO. : 13/640872  
DATED : November 18, 2014  
INVENTOR(S) : Lee et al.

Page 1 of 1

It is certified that error appears in the above-identified patent and that said Letters Patent is hereby corrected as shown below:

In the claims:

Column 20,  
Line 62, "[L]" should read --[L]$^{+}$--.

Column 21,  
Line 6, "SiO$_2$TiO$_2$—MgO" should read --SiO$_2$-TiO$_2$-MgO--.

Signed and Sealed this  
Thirtieth Day of June, 2015

Michelle K. Lee  
*Director of the United States Patent and Trademark Office*